(12) United States Patent
Rosický et al.

(10) Patent No.: US 12,357,478 B2
(45) Date of Patent: Jul. 15, 2025

(54) 3D PRINTED PROSTHETIC SOCKET FOR RESIDUAL LIMB

(71) Applicant: ING Corporation, SPOL. S.R.O., Frýdlant (CZ)

(72) Inventors: Jiří Rosický, Frýdlant (CZ); Tomáš Bouma, Rychvald (CZ); Aleš Grygar, Kopřivnice (CZ)

(73) Assignee: ING Corporation, SPOL. S.R.O., Frýdlant (CZ)

( * ) Notice: Subject to any disclaimer, the term of this patent is extended or adjusted under 35 U.S.C. 154(b) by 656 days.

(21) Appl. No.: 17/635,953

(22) PCT Filed: Aug. 20, 2020

(86) PCT No.: PCT/CZ2020/050056
§ 371 (c)(1),
(2) Date: Feb. 16, 2022

(87) PCT Pub. No.: WO2021/032225
PCT Pub. Date: Feb. 25, 2021

(65) Prior Publication Data
US 2022/0265444 A1  Aug. 25, 2022

(30) Foreign Application Priority Data
Aug. 20, 2019  (CZ) ............................ CZ2019-544

(51) Int. Cl.
*A61F 2/80* (2006.01)
*A61F 2/78* (2006.01)
(Continued)

(52) U.S. Cl.
CPC ............ *A61F 2/80* (2013.01); *A61F 2/7812* (2013.01); *B33Y 80/00* (2014.12);
(Continued)

(58) Field of Classification Search
CPC .................................. A61F 2/80; A61F 2/78
See application file for complete search history.

(56) References Cited

U.S. PATENT DOCUMENTS 7,867,286 B2 * 1/2011 Einarsson ................. A61F 2/78
623/32
11,324,612 B2 * 5/2022 Hansen ..................... A61F 2/80
(Continued)

FOREIGN PATENT DOCUMENTS

| CN | 109199651 A | 1/2019 |
| WO | 2017151577 A1 | 9/2017 |

OTHER PUBLICATIONS

PCT International Search Report in PCT/CZ2020/050056 dated Feb. 9, 2021, 4 pages.

*Primary Examiner* — Bruce E Snow
(74) *Attorney, Agent, or Firm* — Thedford I. Hitaffer; Hitaffer & Hitaffer, PLLC (57) ABSTRACT

The invention is a 3D printed prosthetic socket for a residual limb consisting of a 3D printed shell. The 3D printed prosthetic socket comprises a distal end adapted for linking the interconnecting adapter of the socket and a proximal end with an opening adapted for inserting the limb. The 3D printed shell comprises a first housing of the socket comprising an inner wall and an outer wall, wherein the first housing of the socket comprises a rigid region having, in the direction perpendicular to the inner wall, the rigidity of the rigid region and an elastic region having, in the direction perpendicular to the inner wall the rigidity of the elastic region. The rigidity of the elastic region is smaller than the rigidity of the rigid region, wherein the elastic region comprises a set of shaped openings and is adapted for softening the contact of the residual lower limb with the prosthetic socket, wherein the 3D printed shell is made of a single 3D printed part.

9 Claims, 8 Drawing Sheets

(51) Int. Cl.
 *B33Y 80/00* (2015.01)
 *A61F 2/50* (2006.01)
 *A61F 2/66* (2006.01)

(52) U.S. Cl.
 CPC . *A61F 2002/505* (2013.01); *A61F 2002/6614* (2013.01); *A61F 2002/7837* (2013.01)

(56) References Cited

U.S. PATENT DOCUMENTS

2009/0082877 A1  3/2009 Einarsson
2021/0137707 A1* 5/2021 Hansen .................... A61F 2/78
2022/0265444 A1* 8/2022 Rosický ................ A61F 2/7812
2022/0287857 A1* 9/2022 Rosický ................ A61F 2/5046

* cited by examiner

3D PRINTED PROSTHETIC SOCKET FOR RESIDUAL LIMB

CROSS-REFERENCE TO RELATED APPLICATIONS

This application is the National Stage entry of PCT/CZ2020/050056, filed on Aug. 20, 2020 which claims priority to Czech Patent Application Number PV 2019-544, filed on Aug. 20, 2019, the disclosures of which are incorporated herein by reference in their entireties.

TECHNICAL FIELD

The invention relates to a custom-tailored 3D printed prosthetic socket for a residual limb.

BACKGROUND OF THE INVENTION

High-quality and well-fitting prosthetic sockets are the basis for a comfortable life of a patient with a residual limb. Due to the individual parameters of each residual limb, it is necessary to make prosthetic sockets always tailored for the specific patient. The function of the prosthetic socket is both load-bearing, wherein weight is transferred from the residual limb to the prosthesis itself, and fixating, wherein it is necessary to ensure sufficient adhesion of the socket to the limb, but at the same time the socket needs to be comfortable for the patient. Prosthetic sockets are made with respect to the condition of the residual limb, the physical activity of the patient and their weight. Since these parameters may change at shorter or longer intervals during the patient's life, it is desirable that the manufacture of the prosthetic socket be as simple as possible and thus less expensive.

Most prior art prosthetic sockets are manufactured in two steps. The first step is to create a model of the residual limb, either manually in form of a casting and a physical model of the residual limb, or a digital CAD/CAM model, from which, in the second step, an individual prosthetic socket is created, most often by lamination or thermoplastic shaping. A disadvantage of these solutions is the time-consuming design and manufacture and the limitation of the design embodiment due to the technology used.

Recently, efforts have been made to create 3D printed prosthetic sockets tailored for the patient based on a residual limb scan, a residual limb physical model scan, or residual limb measurements. According to the current state of the art, the digital model of the residual limb is modified in a computer, and on basis thereof, a CAD model of the socket is created, which is then printed on a 3D printer.

The problem of this solution is, on the one hand, the requirement for sufficient strength of the socket, and, on the other hand, the requirement to ensure comfort for the residual limb for all-day wear. Thus, if the socket is to be strong enough to meet the strength standards imposed on sockets, such a socket is uncomfortable for the patient in case of volume changes of the limb.

In the current state of the art, this problem is solved, for example, in patent document US20170246013, in which the prosthetic socket consists of an inner and outer surface, between which there are structural elastic elements allowing to reduce the pressure of the socket material on the residual limb. A disadvantage of this solution is the absence of adaptation of the flexibility of the socket to the specific residual limb, since each portion of the residual limb includes soft tissues and bone structures differently deforming over time.

In the current state of the art, the lightening of a specific portion of the residual limb is solved by inserting soft, for example silicone, pellets to the affected regions. For example, in the patent document US20160228266, the lightening of specific portions of a residual limb is discussed for greater patient comfort when wearing a prosthesis by inserting soft thinned flexible regions of a residual limb sleeve.

In the current state of the art, there is no outer supporting prosthetic socket that would solve the problem of softening a particular region in contact with the residual limb in 3D printed outer supporting prosthetic sockets and that would at the same time meet the requirements for strength, rigidity, and load-bearing capacity.

SUMMARY OF THE INVENTION

The above shortcomings are, to a certain extent, overcome by a 3D printed prosthetic socket according to the present invention that comprises at least a first housing with an outer wall and inner wall that comprises rigid regions and at least one elastic region with a rigidity smaller than the rigidity of the rigid region, which is achieved using shaped openings. In a preferred embodiment, the elastic region is located on at least one residual limb region selected from a set of postero-lateral limb region, postero-medial limb region, posterior limb region, antero-lateral limb region, antero-medial limb region, anterior limb region, medial limb region, lateral limb region. Alternatively, the elastic region is made as a set of at least three elastic elements deformable in the direction away from the contact surface with the residual limb to the inner wall of the first housing.

The shaped openings or elastic elements of the elastic region are arranged such that the value of the Poisson's number of the elastic region is less than zero. This allows the elastic region to expand in all directions simultaneously and provides the residual limb with sufficient comfort. In a preferred embodiment, the prosthetic socket also comprises a second housing located outside of the first housing and connected to the first housing in the proximal and distal region of the socket, wherein an air gap is created between the housings. The first and second housings may be further interconnected by ribs that provide additional strength to the prosthetic socket. To remove supporting or unused printing material during the manufacturing process, the first housing, or the second housing, includes at least one opening.

The 3D printed prosthetic socket according to the present invention comprises a lightened structure in the distal region designed based on at least one parameter from a set including at least weight of the patient, degree of their activity, length of the residual limb, geometry thereof, size of the prosthetic foot, type of the prosthetic foot, and total length of the prosthesis. Since the distal end comprises a significant portion of the volume of the socket, by optimizing the lightened structure, the weight of the entire socket is reduced and thereby the comfort of the patient with the residual limb is increased and material is saved.

The 3D printed prosthetic socket according to the present invention is adapted for connection to the cover of the prosthesis that comprises linking elements from a set of a pin, opening, spring, groove, helix, clamp joint, thread, screw, and rivet.

In another preferred embodiment, the 3D printed prosthetic socket is made of one type of material. Alternatively, the 3D printed prosthetic socket according to this invention may be made from two or more types of materials, wherein in this manner, the rigidity of individual regions of the first housing of the prosthetic socket may be adjusted.

DESCRIPTION OF DRAWINGS

A summary of the invention is further clarified using exemplary embodiments thereof, which are described with reference to the accompanying drawings, in which.

EXEMPLARY EMBODIMENTS OF THE INVENTION

Said embodiments show exemplary variants of the embodiments of the invention, which, however, have no limiting effect on the scope of protection.

Figure 1:
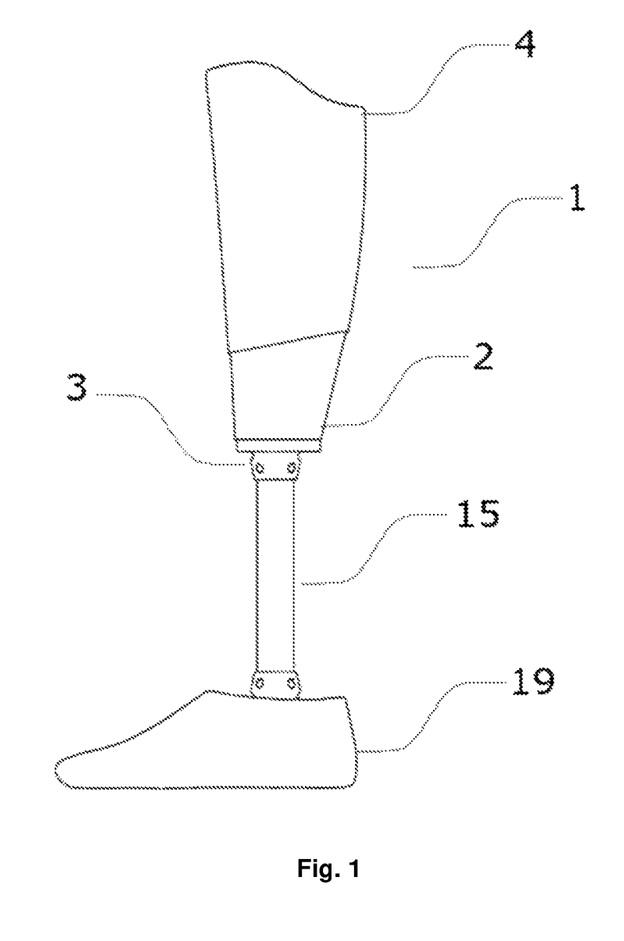
FIG. 1 shows a transtibial prosthesis comprising a 3D printed prosthetic socket and adjoining prosthetic parts.
Figure 2:
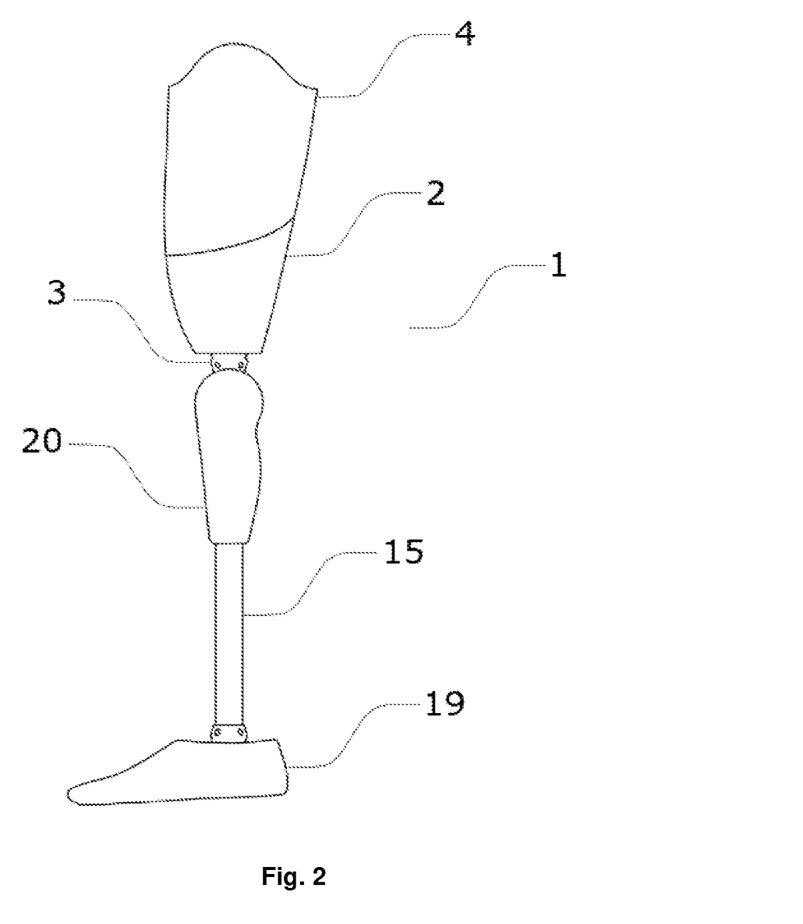
FIG. 2 shows a transfemoral prosthesis comprising a 3D printed prosthetic socket and adjoining prosthetic parts.
Figure 3:
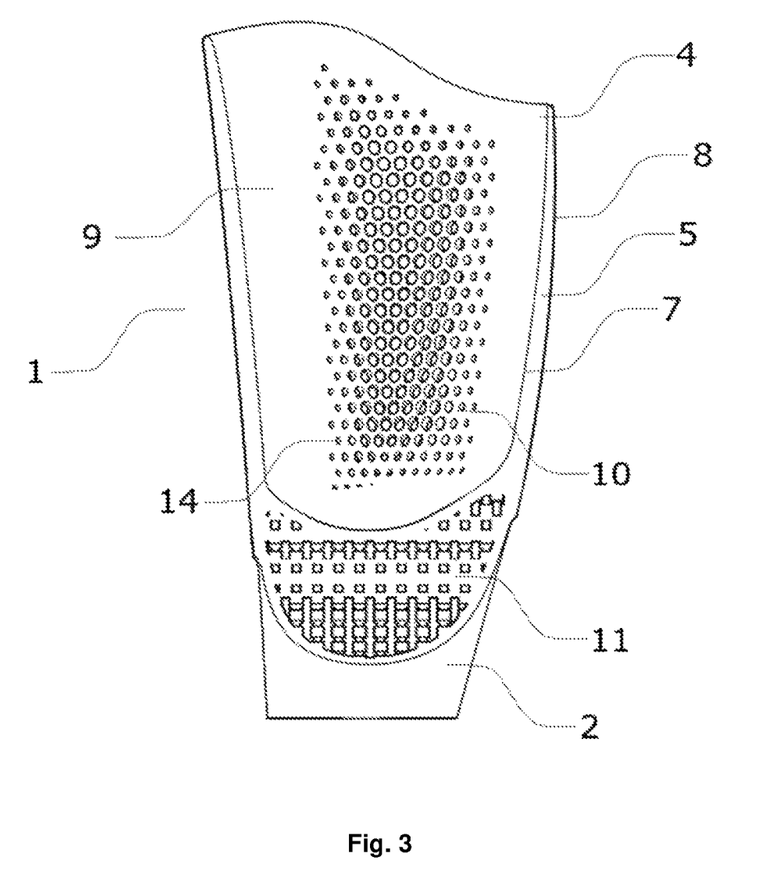
FIG. 3 shows a cross-sectional view of the 3D printed prosthetic socket with the first housing comprising openings in the elastic region, and a lightened distal end structure.
Figure 4:
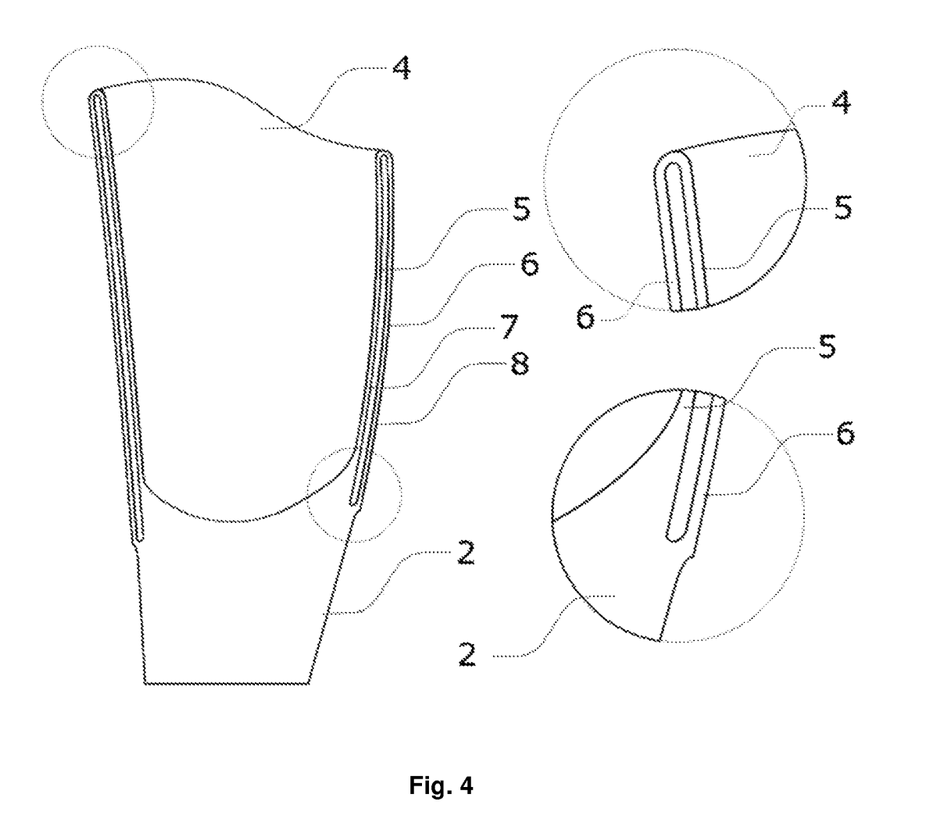
FIG. 4 shows a detail of the arrangement of the second housing to the first housing of the 3D printed prosthetic socket.

The prosthetic socket 1 according to the present invention is, as shown in FIG. 1 and FIG. 2, made of a solid material using the 3D printing technology, thereby creating a continuous and one-part shell with a cavity for the residual limb. In a preferred embodiment, the elastic module of the material used reaches 1,000 to 4,000 MPa at room temperature. Alternatively, the prosthetic socket 1 may be made by simultaneous one-part printing of several types of materials, wherein the materials may pass continuously or in leaps. In this exemplary embodiment, the elastic module of the first material is 1,000 to 4,000 MPa at room temperature and the elastic module of another material is 3 to 200 MPa at room temperature. In another exemplary embodiment, the prosthetic socket 1 is composed of several portions and thus is not made of one-part. In this embodiment, at least two portions of the prosthetic socket 1 are connected and secured by a suitable connecting mechanism, wherein at least one portion of the multi-part prosthetic socket 1 is made by 3D printing technology. The first exemplary embodiment that is shown in FIG. 1 and in FIG. 2, the prosthetic socket 1 comprises a distal end 2 adapted for linking the modular parts 15 of the lower limb prosthesis and a proximal end 4 with an opening for inserting the limb, between which the central portion of the prosthetic socket 1 is located. In another exemplary embodiment, the distal end 2 is adapted for linking the prosthetic knee joint 20. In the exemplary embodiment that is shown in FIG. 3, the central portion is made as containing one housing, i.e. it comprises only the first housing 5. In an alternative embodiment that is shown in FIG. 4, the central portion is made as containing two housings, wherein in a preferred embodiment, the central portion comprises the first housing 5 and the second housing 6, between which a free space enclosed by these housings is located. The minimum thickness of the first housing 5 is 1 mm, the minimum thickness of the second housing 6 is 1 mm, and the minimum distance between the first housing 5 and the second housing 6 is 1 mm. The prosthetic sockets 1 according to the present invention are made on a 3D printer using one of the 3D printing methods: SLA, SLS, FDM, MJF, DLP, 3DP, PJF, CLIP. One or more materials of which the prosthetic socket 1 is made belongs to the set of PA, ABS, PLA, PE, PP, CPP, HPP, TPU, TPE, photopolymers, and other materials suitable for the above-mentioned 3D printing methods. The chosen material may also be reinforced using fibers of glass, carbon, carbon nanofibers, or any other suitable fibers.

Regardless of the embodiment of the central portion, the prosthetic socket 1 comprises an inner wall 7 that is in contact with the limb and has a load-bearing and a lightening function, and a rigid wall 8 that has a load-bearing and aesthetic function and, furthermore, is a representation of the outer shape of the socket of the prosthesis and simultaneously is adapted for shape alignment of the prosthesis with regard to the offset of the limb relative to the axis of the prosthesis. The central longitudinal axis of the inner space of the prosthetic socket 1 corresponds to the axis of the limb, and the central longitudinal axis of the outer surface follows the axis of the prosthesis. The relative position of the axis of the inner space and the axis of the outer space is different in most patients, wherein the central longitudinal axis of the inner space and the central axis of the outer space form an angle from the set of 0° to 90°, but most often 0° to 45°. In some patients, the axes are identical and the solution according to this invention may be applied to these cases as well.

Figure 5:
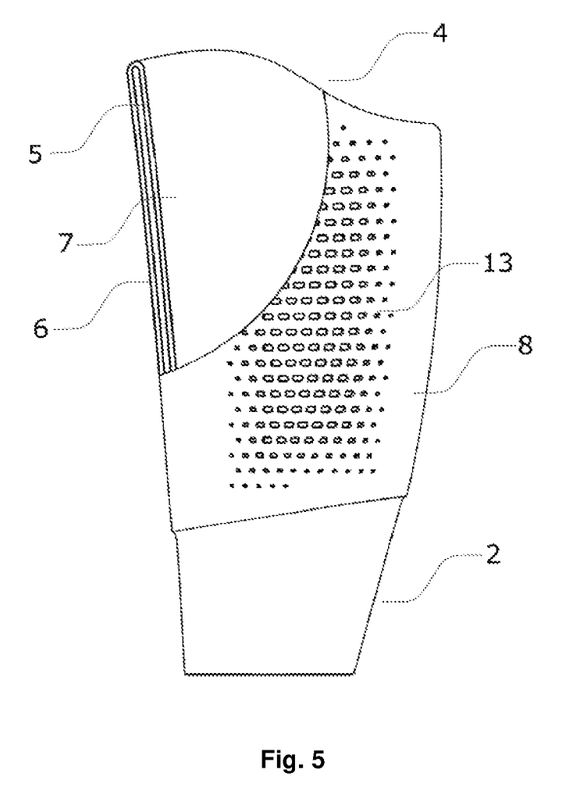
FIG. 5 shows the 3D printed prosthetic socket with two housings and openings of the second housing.

The prosthetic socket 1 is adapted for transferring the load from the limb to the axis of the prosthesis connecting the prosthetic socket 1 to the prosthetic foot 19. Due to the anatomy of the structure of the limb, it is necessary to lighten some of its regions, i.e. allow their shape and volume expansibility and provide space for possible swelling and prevent unwanted soft tissue bruising. This is achieved by including at least one elastic region 10 in the structure of the prosthetic socket 1 that achieves a maximum of 85% of the rigidity of the rigid region 9 at room temperature. In a preferred embodiment, the rigidity of the elastic region 10 is in the range of 5% to 85% of the rigidity of the rigid region 9 at room temperature. In an exemplary embodiment that is shown in FIG. 3, the elastic region 10 of the socket is shown on the posterolateral region of the limb. Alternatively, the prosthetic socket 1 comprises two elastic regions 10, in the posterolateral and posteromedial region. In another exemplary embodiment, the elastic region 10 of the socket may be located in the posterior region, anterior region, medial region, or lateral region. In another exemplary embodiment, the central portion comprises, arbitrarily according to the individual proportions of the patient, the residual limb, or the structure type of the prosthetic socket 1, the elastic regions 10. In another exemplary embodiment, in which the prosthetic socket 1 is made as containing two housings, only the first housing 5 comprises the elastic region 10. In this exemplary embodiment, the second housing 6 is hermetically sealed and its rigidity reaches at least 90% of the rigidity of the material used at room temperature. In an exemplary embodiment shown in FIG. 5, the second housing 6 comprises at least one opening 13 of the second housing that is of any shape, wherein the opening 13 of the second housing is adapted for moisture removal, aeration of the prosthetic socket 1 to the limb, removal of excess material during manufacture, reducing the weight of the second housing 6, or it has an aesthetic function, or it is adapted for placement of a vacuum valve, lock, or another fastening mechanism, or is adapted for any combination of the functions listed.

Figure 8:
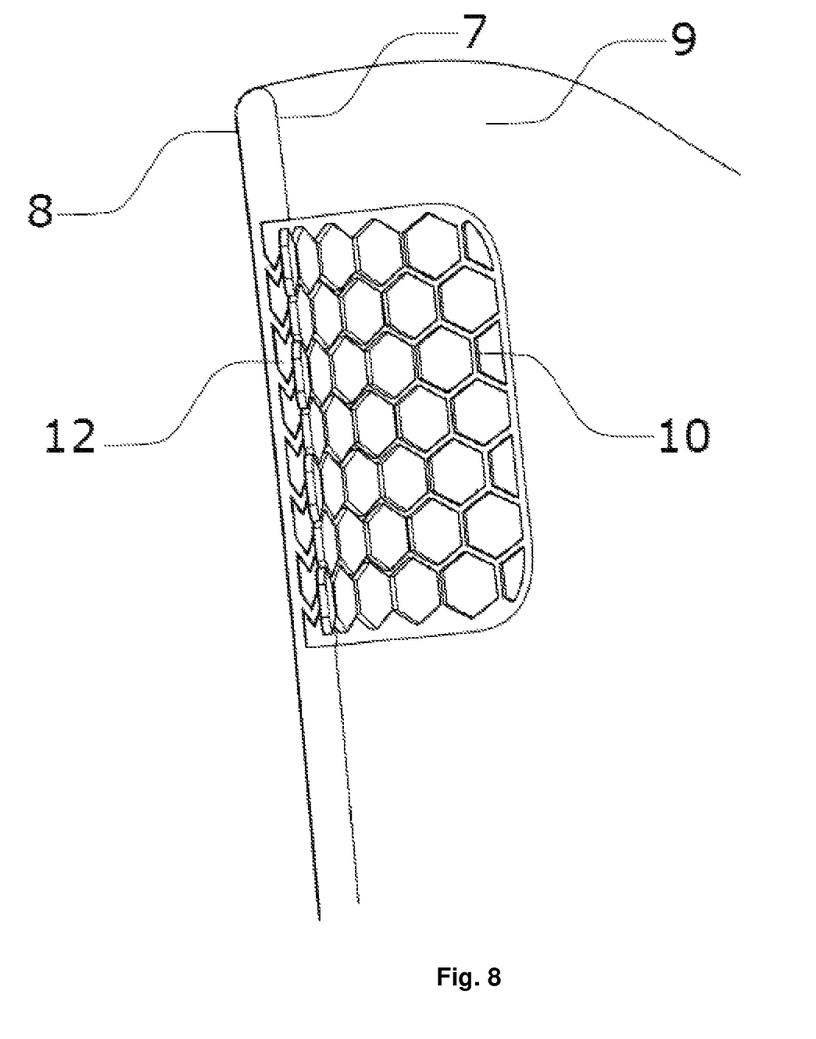
FIG. 8 shows an implementation of the elastic area by means of elastic elements in a recess in the inner wall of the 3D printed prosthetic socket.

In the first exemplary embodiment, the elastic region 10 comprises a set of shaped openings 14. An exemplary embodiment of the shaped openings 14 is shown in FIG. 3, wherein the shaped openings 14 may also be mutually interconnected and thus form more complex shapes. The openings may also have additional other various shapes for a defined purpose. Depending on the specific shape, distance, and size, the shaped openings 14 reduce the rigidity of the elastic region 10 and provide it with directional expansibility. In a preferred embodiment, the elastic region 10 is simultaneously expansible in multiple directions, i.e. it has a negative Poisson's number value. In one of the exemplary embodiments, all shaped openings 14 of the set have the same shape and their size and distance change continuously, wherein their sizes increase towards the centre of the elastic region 10. In alternative embodiments, it is possible to combine different shaped openings 14 and arbitrarily change their size and distance independent of the position in the elastic region 10. Alternatively, it is possible to make the elastic region 10 using a shaped recess in the inner wall 7 of the prosthetic socket 1, as shown in FIG. 8. In this embodiment, elastic elements 12 are located in the recess in the inner wall 7, which, depending on the shape, size, and inner structure, spring under load. In this exemplary embodiment, the required lower rigidity of the prosthetic socket 1 and a lower load on the limb are achieved in the location of the elastic elements 12.

The rigidity of the regions 9, 10 is determined by the specific shape, distance, and size of the shaped openings 14 located in the given region. In the case of the rigid regions 9, the shaped openings 14 are smaller, they have a shape that ensures a greater rigidity of the rigid region 9, and/or they are spaced from each other, or the shaped openings 14 are not located in the rigid regions 9 at all. Using this embodiment of the shaped openings 14, thicker 3D printed structures are achieved that fill the space between the shaped openings 14, while ensuring a higher rigidity of the rigid region 9. By thicker 3D printed structures are meant structures with a larger cross-section at the location between the shaped openings 14 and with a higher volume representation in proportion to the volume representation of the shaped openings 14. In the case of the elastic regions 10, the shaped openings 14 are bigger, they have a shape that ensures a lower rigidity of the elastic region 10, and/or they are located in proximity to each other. Using this embodiment of the shaped openings 14, thinner 3D printed structures are achieved that fill the space between the shaped openings 14, while ensuring a lower rigidity of the elastic region 10. By thinner 3D printed structures are meant structures with a smaller cross-section at the location between the shaped openings 14 and with a lower volume representation in proportion to the volume representation of the shaped openings 14, wherein they supply the required elasticity to the elastic region 10 if the limb in the prosthetic socket 1 exerts force on it.

The transfer of the load at the distal end 2 of the socket of the prosthesis 1 is implemented using a lightened structure 11 shown in FIG. 3. It is designed using a finite element method by calculating the optimal material distribution with respect to the prosthesis geometry and the total transferred load. This load is based on the individual parameters of each patient, wherein the individual parameters are from a set comprising at least the patient's weight, physical activity, length of the limb, limb geometry, size of the prosthetic foot 19, type of the prosthetic foot 19, and the total length of the prosthesis that comprises the prosthetic socket 1, a linking adapter 3, modular parts 15 of the prosthesis, and the prosthetic foot 19, wherein in another exemplary embodiment, it also comprises the cover 17 of the prosthesis. In another exemplary embodiment, the prosthesis also includes the knee joint 20. The embodiment of the lightened structure 11 itself is designed also with regard to the need of removal of unnecessary material after the 3D printing, therefore, it does not comprise any enclosed space from which unused printing material could not be removed after manufacture.

The distal end 2 of the prosthetic socket 1 is adapted for linking the linking adapter 3, wherein the linking adapter 3 is further connected to the modular parts 15 of the prosthesis which are further connected to the prosthetic foot 19. In a preferred embodiment, the linking adapter 3 is firmly connected to the prosthetic socket 1, wherein the modular parts 15 of the prosthesis are detachably linked to the linking adapter 3. The linking adapter 3 may be linked to the 3D printed prosthetic socket 1 using, for example, screws, snap-in mechanism, or thread, where the 3D printed prosthetic socket 1 comprises an outer thread and the linking adapter 3 comprises an inner thread, or the 3D printed prosthetic socket 1 comprises an inner thread and the linking adapter 3 comprises an outer thread.

In the first exemplary embodiment, the prosthetic socket 1 is linked to the other portions of the prosthesis using a screw connection, wherein in this exemplary embodiment, the distal end 2 contains at least one opening for the thread. Alternatively, other structural joints may be used, such as, for example, nails, threaded inserts, pins, screws, lamellae, connecting fittings, or also gluing.

Figure 6:
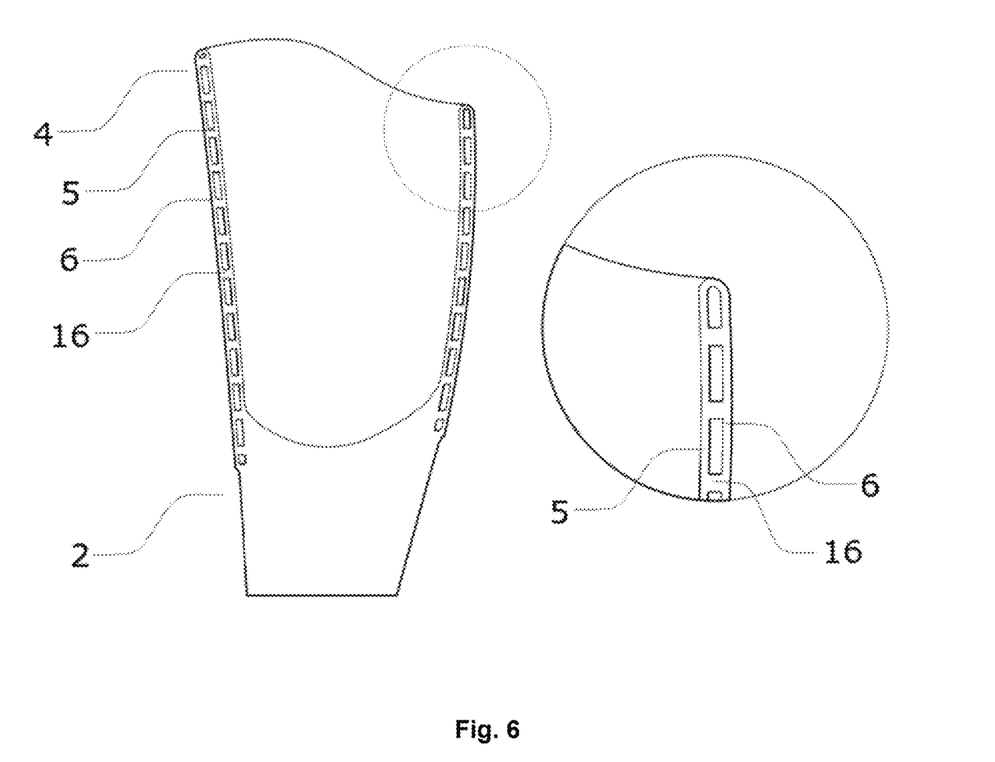
FIG. 6 shows an example of the location of the ribs between the first and the second housing of the 3D printed prosthetic housing.

In one of the exemplary embodiments, the prosthetic socket 1 comprises the distal end 2 and the proximal end 4, between which a central portion is located comprising the first housing 5 and the second housing 6. In this exemplary embodiment, between the first housing 5 and the second housing 6, a reinforcing structure composed of ribs 16 is located, as is shown in FIG. 6.

Figure 7:
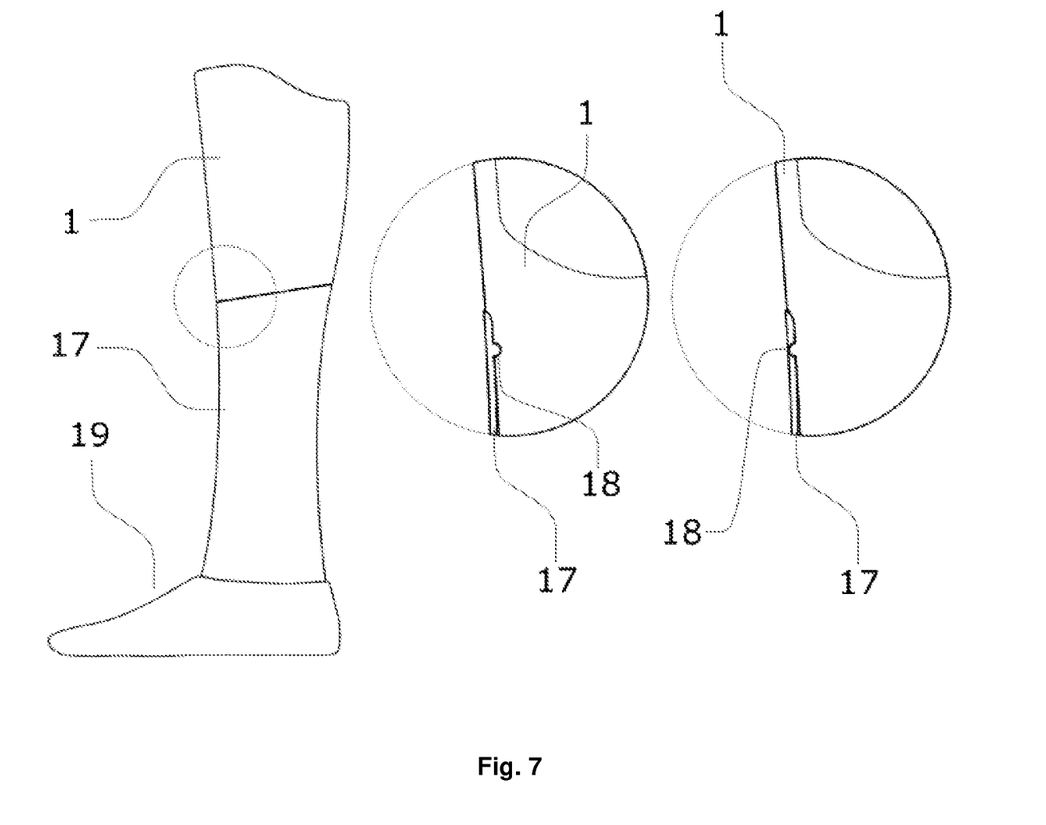
FIG. 7 shows a detail of the link of the cover of the prosthesis to the 3D printed prosthetic socket.

In an exemplary embodiment shown in FIG. 7, an assembly of the prosthetic socket 1 with the cover 17 of the prosthesis is shown. In this exemplary embodiment, the prosthetic socket 1 comprises a linking element 18 for linking the cover 17 of the prosthesis. The cover 17 of the prosthesis is continuous and one-part and is made of a solid or elastic material using the 3D printing technology. The function of the cover 17 of the prosthesis is aesthetic, wherein it covers the modular parts 15 of the prosthesis, in another exemplary embodiment, it also covers the knee joint 20. In this exemplary embodiment, the cover 17 of the prosthesis comprises, from the inner side of the edge for linking to the prosthetic socket 1, at least one element adapted for connecting to the linking element 18, wherein it is an opening, groove, or any other element corresponding, in terms of its shape, to the outer surface of the linking element 18. In this exemplary embodiment, the linking element 18 is a pin of approximately cylindrical shape, perpendicular to the inner wall 7 of the cover 17 of the prosthesis. Alternatively, the linking element 18 is embodied as a spring, clamp, at least 1 mm high edge, perpendicular to the inner wall 7 of the cover 17 of the prosthesis, diminishingly tapered edge of the cover 17 of the prosthesis, or as any other suitable dismountable joint. In this exemplary embodiment, the prosthetic socket 1 comprises a recess corresponding to the size and thickness of the edge of the wall of the cover 17 of the prosthesis, wherein their connection creates a seamless joint that does not create any overlap between the socket 1 and the cover 17 of the prosthesis.

The manufacture of the 3D printed prosthetic socket 1 according to the present invention is implemented using a system of a communicatively interconnected 3D scanner, computer device, and 3D printer, and it comprises a step of obtaining the digital image of the residual limb, step of adjusting the area of the digital image of the residual limb, and a design of the shell of the prosthetic socket 1, and a step of manufacturing the prosthetic socket 1 on a 3D printer.

LIST OF REFERENCE NUMBERS

1—prosthetic socket
2—distal end
3—linking adapter
4—proximal end
5—first housing
6—second housing
7—inner wall
8—outer wall
9—rigid region
10—elastic region
11—lightened structure
12—elastic element
13—opening of the second housing
14—shaped opening
15—modular parts of the prosthesis
16—ribs
17—cover of the prosthesis
18—linking element
19—prosthetic foot
20—prosthetic knee joint

What is claimed is:

1. A 3D printed prosthetic socket for a residual lower limb consisting of a 3D printed shell comprising a distal end adapted for linking an interconnecting adapter of the prosthetic socket and a proximal end with an opening adapted for inserting the residual lower limb, wherein the shell comprises a first housing of the prosthetic socket comprising an inner wall and an outer wall, wherein the first housing of the prosthetic socket comprises a rigid region having, in the direction perpendicular to the inner wall, the rigidity of the rigid region and an elastic region having, in the direction perpendicular to the inner wall, the rigidity of the elastic region, wherein the rigidity of the elastic region under a load is smaller than the rigidity of the rigid region, wherein the elastic region comprises a set of shaped openings and is adapted for softening the contact of the residual lower limb with the prosthetic socket, wherein the elastic region takes Poisson's number values lower than zero, and wherein the elastic region is located in at least one region of the prosthetic socket from the following set: postero-lateral limb region, postero-medial limb region, posterior limb region, antero-lateral, antero-medial, anterior limb region, medial, lateral.

2. The 3D printed prosthetic socket for a residual lower limb according to claim 1, wherein between the distal end and the proximal end, the shell further comprises the second housing located outside of the first housing, wherein between the first housing and second housing there is an air gap.

3. The 3D printed prosthetic socket for a residual lower limb according to claim 2, wherein it further comprises at least two shaped openings in the elastic region of the first housing and at least one opening of the second housing.

4. The 3D printed prosthetic socket for a residual lower limb according to claim 3, wherein in the space between the rigid region of the first housing and the second housing, there is a set of ribs interconnecting the first housing and the second housing, wherein between the ribs there is an air gap that is permeably connected to at least one opening from the set of: opening of the second housing and shaped opening of the elastic region.

5. A 3D printed prosthetic socket for a residual lower limb consisting of a 3D printed shell comprising a distal end adapted for linking an interconnecting adapter of the prosthetic socket and a proximal end with an opening adapted for inserting the residual lower limb, wherein the shell comprises a first housing of the prosthetic socket comprising an inner wall and an outer wall, wherein the first housing of the prosthetic socket comprises a rigid region having, in the direction perpendicular to the inner wall, the rigidity of the rigid region and an elastic region having, in the direction perpendicular to the inner wall, the rigidity of the elastic region, wherein the rigidity of the elastic region under a load is smaller than the rigidity of the rigid region, wherein the elastic region is adapted for softening the contact of the residual lower limb with the prosthetic socket and comprises at least one shaped recess in the inner wall of the first housing comprising a set of at least three elastic elements, wherein the at least three elastic elements are connected to the shaped recess and are provided with a contact surface, wherein the elastic elements are elastically deformable in the direction from the inner wall to the outer wall of the first housing, wherein the shell further comprises, between the distal end and the proximal end, the second housing located outside the first housing, wherein between the first housing and second housing, there is an air gap, wherein the second housing comprises at least one opening of the second housing.

6. The 3D printed prosthetic socket for a residual lower limb according to claim 5, wherein the set of at least three elastic elements is located in at least one region of the prosthetic socket from the following set: postero-lateral limb region, postero-medial limb region, posterior limb region, antero-lateral limb region, antero-medial limb region, anterior limb region, medial limb region, lateral limb region.

7. The 3D printed prosthetic socket for a residual lower limb according to claim 5, wherein in the space between the rigid region of the first housing and the second housing, there is a set of ribs interconnecting the first housing and the second housing, wherein between the ribs, there is an air gap that is permeably connected to at least one opening of the second housing.

8. The 3D printed prosthetic socket for a residual lower limb according to claim 1, wherein the shell of the prosthetic socket is made of one type of material.

9. An assembly of the 3D printed prosthetic socket for a residual lower limb according to claim 1 and a cover of the prosthesis comprising linking elements from the inner wall of the cover of the prosthesis, wherein the linking element for linking the cover of the prosthesis to the prosthetic socket is selected from a set of pin, opening, spring, groove, outer helix, inner helix, clamp joint, thread, screw, and interconnecting rivet, and wherein the prosthetic socket is adapted for connection to the linking element.

* * * * *